United States Patent
Palaniswamy et al.

(10) Patent No.: US 10,324,097 B2
(45) Date of Patent: Jun. 18, 2019

(54) SYSTEM AND METHODS FOR BILIRUBIN ANALYSIS

(71) Applicant: Neolight LLC, Scottsdale, AZ (US)

(72) Inventors: Sivakumar Palaniswamy, Chandler, AZ (US); Deepakshyam Krishnaraju, Tempe, AZ (US); Martin Peacock, Royston (GB)

(73) Assignee: Neolight LLC, Scottsdale, AZ (US)

( * ) Notice: Subject to any disclaimer, the term of this patent is extended or adjusted under 35 U.S.C. 154(b) by 0 days.

(21) Appl. No.: 15/954,360

(22) Filed: Apr. 16, 2018

(65) Prior Publication Data

US 2019/0064190 A1 Feb. 28, 2019

Related U.S. Application Data

(60) Provisional application No. 62/552,226, filed on Aug. 30, 2017.

(51) Int. Cl.
  *G01N 33/72* (2006.01)
  *G01N 33/49* (2006.01)
  (Continued)

(52) U.S. Cl.
  CPC ...... *G01N 33/728* (2013.01); *B01L 3/502715* (2013.01); *G01N 27/308* (2013.01); *G01N 27/3277* (2013.01); *G01N 27/48* (2013.01); *G01N 33/49* (2013.01); *B01L 2200/04* (2013.01); *B01L 2200/16* (2013.01); *B01L 2300/021* (2013.01);
  (Continued)

(58) Field of Classification Search
  None
  See application file for complete search history.

(56) References Cited

U.S. PATENT DOCUMENTS

| | | |
|---|---|---|
| 4,204,839 A | 5/1980 | Wu et al. |
| 4,311,665 A | 1/1982 | Wu |

(Continued)

FOREIGN PATENT DOCUMENTS

| | | |
|---|---|---|
| WO | 9106868 A1 | 5/1991 |
| WO | 2016038505 A2 | 3/2016 |
| WO | 2016193996 A1 | 12/2016 |

OTHER PUBLICATIONS

Kim, B.B. et al. Bromophenol Blue Binding to Mammalian Albumins and Displacement of Albumin-Bound Bilirubin, 2008, Pakistan Journal of Biological Sciences, vol. 11(20), pp. 2418-2422, 2008.*

(Continued)

*Primary Examiner* — Xiaoyun R Xu
(74) *Attorney, Agent, or Firm* — Quarles & Brady LLP (57) ABSTRACT

A method for measuring bilirubin levels in a subject. The method can include the steps of providing a sample to be measured from the subject, wherein the sample comprises bilirubin bound to albumin; adding a release agent to the sample, the release agent configured to release the bound bilirubin from the albumin; measuring electrochemical data of the sample using an electrochemical cell; and determining a total serum bilirubin concentration of the sample using the electrochemical data. This method is capable of providing a simpler, faster, and more robust measurement when compared to traditional bilirubin assay methods.

20 Claims, 5 Drawing Sheets

(51) Int. Cl.
- B01L 3/00 (2006.01)
- G01N 27/48 (2006.01)
- G01N 27/30 (2006.01)
- G01N 27/327 (2006.01)

(52) U.S. Cl.
CPC ............ B01L 2300/0645 (2013.01); B01L 2300/0681 (2013.01); B01L 2300/18 (2013.01); G01N 2800/085 (2013.01); G01N 2800/52 (2013.01)

(56) References Cited

U.S. PATENT DOCUMENTS

| | | |
|---|---|---|
| 7,749,766 B2 | 7/2010 | Pei et al. |
| 8,649,840 B2 | 2/2014 | Sheppard, Jr. et al. |
| 9,194,859 B2 | 11/2015 | Emeric et al. |
| 9,508,673 B2 | 11/2016 | Lin |
| 9,562,874 B2 | 2/2017 | Martin et al. |
| 9,891,215 B2 | 2/2018 | Kayyem et al. |
| 2008/0169206 A1 | 7/2008 | Pei et al. |
| 2010/0224488 A1 | 9/2010 | Pei et al. |
| 2013/0162981 A1 | 6/2013 | Emeric et al. |
| 2014/0262776 A1 | 9/2014 | Martin et al. |
| 2014/0323326 A1 | 10/2014 | Kayyem et al. |
| 2016/0077037 A1 | 3/2016 | Cha et al. |

OTHER PUBLICATIONS

Balamurugan, T. et al. Non-enzymatic detection of bilirubin based on a graphene-polystyrene sulfonate composite, 2015, RSC Advances, vol. 5, pp. 50470-50477, 2015.*

Li, M. et al. Recent developments and applications of screen-printed electrodes in environmental assays—A review, Analytica Chimica Acta, vol. 734, pp. 31-44 (Year: 2012).*

Ahlfors, Criteria for Exchange Transfusion in Jaundiced Newborns, Pediatrics, 1994, 93(3):488-494.

Alves-Dunkerson, et al., Cost Analysis of a Neonatal Point-of-Care Monitor, Am. J. Clin. Pathol., 2002, 117:809-818.

American Academy of Pediatrics Subcommittee on Hyperbilirubinemia, Management of Hyperbilirubinemia in the Newborn Infant 35 or More Weeks of Gestation, Pediatrics, 2004, 114(1):297-316.

Ardakani, et al., Bilirubin/Albumin Ratio for Predicting Acute Bilirubin-Induced Neurologic Dysfunction, Iranian Journal of Pediatrics, 2011, 21(1):28-32.

Avan, et al., Voltammetric Sensing of Bilirubin Based on Nafion/Electrochemically Reduced Graphene Oxide Composite Modified Glassy Carbon Electrode, Current Analytical Chemistry, 2015, 11:96-103.

Bae, et al., Amperometric Determination of Bilirubin with Flow Injection Analysis System, Analytical Letters, 1995, 28(10):1775-1783.

Balamurugan, et al., Non-Enzymatic Detection of Bilirubin Based on a Graphene-Polystyrene Sulfonate Composite, RSC Advances, 2015, 5(62):50470-50477.

Bergmeyer, et al., International Federation of Clinical Chemistry (IFCC) Scientific Committee, Approved Recommendation (1985) on IFCC Methods for the Measurement of Catalytic Concentration of Enzymes, Journal of Clinical Chemistry and Clinical Biochemistry, 1986, 24(7):481-495.

Besser, et al., Yield of Recommended Blood Tests for Neonates Requiring Phototherapy for Hyperbilirubinemia, IMAJ-Israel Medical Association Journal, 2010, 12(4):220-224.

Bhutani, et al., Predictive Ability of a Predischarge Hour-Specific Serum Bilirubin for Subsequent Significant Hyperbilirubinemia in Healthy Term and Near-Term Newborns, Pediatrics, 1999, 103(1):6-14.

Bhutani, et al., Kernicterus: Lessons for the Future From a Current Tragedy, NeoReviews, 2003, 4(2):e30-e32.

Bhutani, et al., Universal Bilirubin Screening for Severe Neonatal Hyperbilirubinemia, Journal of Perinatology, 2010, 30:S6-S15.

Bhutani, et al., Phototherapy to Prevent Severe Neonatal Hyperbilirubinemia in the Newborn Infant 35 or More Weeks of Gestation, Pediatrics, 2011, 128:e1046-e1052.

Burke, et al., Trends in Hospitalizations for Neonatal Jaundice and Kernicterus in the United States, 1988-2005, Pediatrics, 2009, 123(2):524-532.

Chou, et al., Management of Hyperbilirubinemia in Newborns: Measuring Performance by Using a Benchmarking Model, Pediatrics, 2003, 112(6):1264-1273.

Chuang, et al., An Electrochemical Tyrosinase-Immobilized Biosensor for Albumin—Toward a Potential Total Protein Measurement, Sensors and Actuators B, 2006, 114:357-363.

Davis, et al., Interpreting Conjugated Bilirubin Levels in Newborns, Journal of Pediatrics, 2011, 158(4):562-565.

De Luca, NICE Guidelines on Neonatal Jaundice: At Risk of Being Too Nice, The Lancet, 2010, 376(9743):771.

Doumas, et al., Measurement of Direct Bilirubin by Use of Bilirubin Oxidase, Clinical Chemistry, 1987, 33(8):1349-1353.

Fasano, et al., The Extraordinary Ligand Binding Properties of Human Serum Albumin, IUBMB Life, 2005, 57(12)187-796.

Feng, et al. Synthesis of the Multi-Walled Carbon Nanotubes-COOH/Graphene/Gold Nanoparticles Nanocomposite for Simple Determination of Bilirubin in Human Blood Serum, Sensors and Actuators B: Chemical, 2013, 185:337-344.

Filik, et al., Nafion/Multi-Wall Carbon Nanotubes Composite Modified Glassy Carbon Electrode for Sensitive Determination of Bilirubin, Current Nanoscience, 2015, 11(6):784-791.

Fortuney, et al., Enzyme Electrode for the Determination of Bilirubin, Electroanalysis, 1996, 8(3):229-232.

Fossati, et al., One-Step Protocol for Assays of Total and Direct Bilirubin with Stable Combined Reagents, Clinical Chemistry, 1989, 35(1):173-176.

Friedberg, et al., The Origin of Reference Intervals, A College of American Pathologists Q-Probes Study of "Normal Ranges" Used in 163 Clinical Laboratories, Arch. Pathol. Lab. Med., 2007, 131:348-357.

Fukuko, et al., Determination of Total and Direct Bilirubins in Serum with Sodium Dodecyl Sulfate as an Accelerator, Clinica Chimica Acta, 1978, 88(1):149-153.

Grohmann, et al., Bilirubin Measurement for Neonates: Comparison of 9 Frequently Used Methods, Pediatrics, 2006, 117(4):1174-1183.

Holland, et al., Implementing and Validating Transcutaneous Bilirubinometry for Neonates, Am. J. Clin. Pathol., 2009, 132:555-561.

Howanitz, Quality Assurance Measurements in Departments of Pathology and Laboratory Medicine, Arch. Pathol. Lab. Med., 1990, 114(11):1131-1135.

Iskander, et al., Serum Bilirubin and Bilirubin/Albumin Ratio as Predictors of Bilirubin Encephalopathy, Pediatrics, 2014, 134:e1330-e1339.

Jacobsen, et al., Albumin-Bilirubin Binding Mechanism, Journal of Biological Chemistry, 1983, 258(10):6319-6326.

Kannan, et al., Highly Sensitive Amperometric Detection of Bilirubin Using Enzyme and Gold Nanoparticles on sol-gel Film Modified Electrode, Talanta, 2011, 86:400-407.

Keren, et al., A Comparison of Alternative Risk-Assessment Strategies for Predicting Significant Neonatal Hyperbilirubinemia in Term and Near-Term Infants, Pediatrics, 2008, 121(1):e170-e179.

Kim, et al., Bromophenol Blue Binding to Mammalian Albumins and Displacement of Albumin-Bound Bilirubin, Pakistan Journal of Biological Sciences, 2008, 11(20):2418-2422.

Kirk, Neonatal Jaundice: A Critical Review of the Role and Practice of Bilirubin Analysis, Annals of Clinical Biochemistry, 2008, 45:452-462.

Klemm, et al., An Enzymic Method for the Determination of Bilirubin Using an Oxygen Electrode, Electroanalysis, 2000, 12(4):292-295.

Koch, et al., Feasibility of Measuring Free and Total Bilirubin Electrochemically in Serum, Clinical Chemistry, 1981, 27(7):1295-1299.

Kurosaka, et al., A New Enzymatic Assay for Selectively Measuring Conjugated Bilirubin Concentration in Serum with Use of Bilirubin Oxidase, Clinica Chimica Acta, 1998, 269(2):125-136.

(56) References Cited

OTHER PUBLICATIONS

Lee, et al., Association Between Duration of Neonatal Hospital Stay and Readmission Rate, Journal of Pediatrics, 1995, 127(5):758-766.
Li, et al. A Fiber Optic Sensor for Rapid Analysis of Bilirubin in Serum, Analytica Chimica Acta, 1997, 353(2-3):263-273.
Liu, et al., Increased Neonatal Readmission Rate Associated with Decreased Length of Hospital Stay at Birth in Canada, Canadian Journal of Public Health, 2000, 91(1):46-50.
Lu, et al., Determination of Total Bilirubin in Human Serum by Chemiluminescence from the Reaction of Bilirubin and Peroxynante, Talanta, 2004, 63:333-337.
Maisels, Screening and Early Postnatal Management Strategies to Prevent Hazardous Hyperbilirubinemia in Newborns of 35 or More Weeks of Gestation, Seminars in Fetal & Neonatal Medicine, 2010, 15(3):129-135.
Manning, et al., Prospective Surveillance Study of Severe Hyperbilirubinaemia in the Newborn in the UK and Ireland, Archives of Disease in Childhood Fetal and Neonatal Edition, 2007, 92(5):F342-F346.
Metcalfe, et al., Proportion of Neonatal Readmission Attributed to Length of Stay for Childbirth: A Population-Based Cohort Study, BMJ Open, 2016, 6(9):e012007, 7 pages.
Moussa, et al., Electrochemical Oxidation of Bilirubin and Biliverdin in Dimethyl Sulfoxide, Analytical Chemistry, 1988, 60(11):1179-1185.
Murli, et al., Reliability of Transcutaneous Bilirubinometry from Shielded Skin in Neonates Receiving Phototherapy: A Prospective Cohort Study, Journal of Perinatology, 2017, 37:182-187.
Nice, Detection and Treatment of Neonatal Jaundice, The Lancet, 2010, 375(9729):1845.
Niu, et al., The Electrooxidation Behavior of Bilirubin in DMF and DMF + H2O Mixed Solvent, Chinese Journal of Chemistry, 1994, 12(1):1-10.
Noh, et al., Selective Nonenzymatic Bilirubin Detection in Blood Samples Using a Nation/Mn—Cu Sensor, Biosensors and Bioelectronics, 2014, 61:554-561.
O'Leary, et al., A Robust Procedure for the Automated Measurement of Total Serum Bilirubin Using Potassium Ferricyanide, Annals of Clinical Biochemistry, 1993, 30:175-179.
Pearlman, et al., Detection and Measurement of Total Bilirubin in Serum, With Use of Surfactants as Solubilizing Agents, Clinical Chemistry, 1974, 20(4):447-453.
Puppalwar, et al., Review on "Evolution of Methods of Bilirubin Estimation", IOSR Journal of Dental and Medical Sciences, 2012, 1(3):17-28.
Rahman, et al., An Amperometric Bilirubin Biosensor Based on a Conductive Poly-Terthiophene-Mn(II) Complex, Biosensors and Bioelectronics, 2008, 23:857-864.
Ramachandrappa, et al., Health Issues of the Late Preterm Infant, Pediatr Clin N Am, 2009, 56(3):565-577.
Randev, et al., Predicting Neonatal Hyperbilirubinemia Using First Day Serum Bilirubin Levels, Indian Journal of Pediatncs, 2010, 77(2):147-150.
Reddy, et al., Delivery Indications at Late-Preterm Gestations and Infant Mortality Rates in the United States, Pediatrics, 2009, 124(1):234-240.
Rennie, et al., Neonatal Jaundice: Summary of NICE Guidance, BMJ, 2010, 340:1190-1196.
Robertson, et al., Comparison of the Bilirubin Concentration and the Bilirubin/Albumin Ratio with the Bilirubin-Binding Ability in Neonatal Serum, Journal of Pediatrics, 1998, 132(2):343-344.
Roca, et al., Factors Affecting the Binding of Bilirubin to Serum Albumins: Validation and Application of the Peroxidase Method, Pediatric Research, 2006, 60(6):724-728.
Rohle, et al., External Quality Control in the Determination of Neonatal Bilirubin, An Approach to the Improvement of Results, Journal of Clinical Chemistry and Clinical Biochemistry, 1988, 26:441-446.
Serebryakova, et al., Kinetics and Mechanism of Bilirubin Oxidation by Benzoyl Peroxide in Dimethyl Sulfoxide, International Journal of Chemical Kinetics, 2015, 47(1):27-35.
Shoham, et al., A Bilirubin Biosensor Based on a Multilayer Network Enzyme Electrode, Biosensors and Bioelectronics, 1995, 10(3-4):341-352.
Silvestrini, et al., Pyrolyzed Photoresist Carbon Electrodes in Aprotic Solvent: Bilirubin Electrochemistry and Interaction with Electrogenerated Superoxide, Electrochimica Acta, 2014, 147:401-407.
Smitherman, et al., Early Recognition of Neonatal Hyperbilirubinemia and Its Emergent Management, Seminars in Fetal & Neonatal Medicine, 2006, 11(3):214-224.
Steffensrud, et al., Hyperbilirubinemia in Term and Near-Term Infants: Kernicterus on the Rise?, Newborn and Infant Nursing Reviews, 2004, 4(4):191-200.
Taurino, et al., Multiwalled Carbon Nanotubes for Amperometric Array-Based Biosensors, BioNanoScience, 2012, 2(4):185-195.
Thangamuthu, et al., Electrochemical Sensor for Bilirubin Detection Using Screen Printed Electrodes Functionalized with Carbon Nanotubes and Graphene, Sensors, 2018, 18:800, 12 pages.
Thiessen, et al., Displacement of Albumin-Bound Bilirubin by Fatty Acids, Acta Paediat Scand, 1972, 61:285-288.
Trivedi, On the Role of Lysine Residues in the Bromophenol Blue-Albumin Interaction, Italian Journal of Biochemistry, 1997, 46(2):67-73.
Urien, et al., Characterization of Discrete Classes of Binding Sites of Human Serum Albumin by Application of Thermodynamic Principles, Biochemical Journal, 1994, 302(1):69-72.
Watson, Analytic Methods for Bilirubin in Blood Plasma, Clinical Chemistry, 1961, 7(6):603-625.
Widness, et al., Changing Patterns of Red Blood Cell Transfusion in Very Low Birth Weight Infants, Journal of Pediatrics, 1996, 129(5):680-687.
Wang, et al., Determination of Bilirubin by Adsorptive Stripping Voltammetry, Journal of Electroanalytical Chemistry, 1985, 185(1):61-71.
Wang, et al., A Polishable Amperometric Biosensor for Bilirubin, Electroanalysis, 1990, 2(8):647-650.
Wang, et al., Electrocatalytic Oxidation of Bilirubin at Ferrocenecarboxamide Modified MWCNT—Gold Nanocomposite Electrodes, Microchimica Acta, 2009, 164:113-118.
Wu, et al., The Ektachem(R) Clinical Chemistry Slide for Simultaneous Determination of Unconjugated and Sugar-Conjugated Bilirubin, Clinical Chemistry, 1984, 30(8):1304-1309.
Yang, et al., Piezoelectric Detection of Bilirubin Based on Bilirubin-Imprinted Titania Film Electrode, Analytical Biochemistry, 2012, 421(1):37-42.
Young, Preanalytical Issues in Neonatology, www.acutecaretesting. org, Jan. 2002, 5 pages.
Zelenka, et al., Highly Sensitive Method for Quantitative Determination of Bilirubin in Biological Fluids and Tissues, Journal of Chromatography B, 2008, 867(1):37-42.
Andreu, et al., Determination of Direct-Bilirubin by a Fluorimetric-Enzymatic Method Based on Bilirubin Oxidase, Fresenius J Anal Chem, 2000, 368:516-521.
Lojou, et al., Application of the Electrochemical Concepts and Techniques to Amperometric Biosensor Devices, J Electroceram, 2006, 16:79-91.

* cited by examiner

SYSTEM AND METHODS FOR BILIRUBIN ANALYSIS

CROSS-REFERENCE TO RELATED APPLICATIONS

This application claims the benefit of U.S. Provisional Patent Application Ser. No. 62/552,226, filed on Aug. 30, 2017, and entitled "SYSTEMS AND METHODS FOR JAUNDICE DETECTION."

BACKGROUND

Neonatal jaundice is one of the most common physiological manifestations in newborns; the illness presents itself in nearly 60% of term neonates and in 80% of preterm neonates. The illness is a primary reason for high re-admission rates because of its delayed onset. Jaundice is generally benign as its part of the physiological evolution process of neonate's hepatic system, but incorrect or delayed diagnosis can lead to severe brain damage, causing cerebral palsy or kernicterus. Accurate estimation of jaundice is essential for proper intervention and to prevent the development of jaundice into severe hyperbilirubinemia, especially with a growing number of babies being discharged early and sent home.

In the body, because of the large number of potentially reactive groups in bilirubin, very little bilirubin exists free in circulation. Most of these derivatives rapidly associate with albumin, through a network of reversible hydrogen bonds. Together, free- and albumin-bound bilirubin are referred to as unconjugated bilirubin also known as α-bilirubin. Unconjugated bilirubin on reaching the liver, is covalently conjugated to glucuronic acid forming mono and diglucuronides (β and γ bilirubin) not bound to albumin, collectively known as conjugated bilirubin. The water-soluble bilirubin glucuronides are excreted through feces and urine, while a portion gets reabsorbed in duodenum contributing to the enterohepatic circulation. Note, irreversible binding can also occur, and it is now known that in some jaundiced patients' conjugated bilirubin is present in the serum covalently bound to albumin. This species has been called δ-bilirubin.

Free bilirubin (unconjugated and unbound to albumin) is the suspected as being the only form in which bilirubin can cross the intact blood-brain barrier. In clinical practice, the concentration of total bilirubin in neonates is usually equal to unconjugated bilirubin. Total bilirubin is used as an easily measured proxy for the concentration of unconjugated bilirubin, and hence the risk of bilirubin induced neurotoxicity (BIND) or kernicterus. Although, excess levels of conjugated bilirubin and δ-bilirubin can cause conjugated hyperbilirubinemia and cholestatic jaundice, respectively, it's extremely rare in neonates. Unconjugated hyperbilirubinemia is more common condition as it is a consequence of physiological development of the hepatic system.

Preventing newborns from toxic bilirubin levels has been one of the prime concerns for pediatricians. Currently tools like a nomogram, used for plotting hour specific total serum bilirubin levels vs. age of newborns, are employed to understand the trend of the blood bilirubin levels and potential risk of developing hyper-bilirubinemia prior to discharge. Bhutani's nomogram is the industry standard and has been recommended by both AAP and NICE for the same purpose.

In current practice, using isolated risk factors as a measure to predict the subsequent development of hyperbilirubinemia in early discharged newborns has been largely unsuccessful. On top of that, transcutaneous bilirubin (TcB) measurement, used for screening neonates and preferred for their noninvasiveness, can be confounded by the discrepancies between total serum bilirubin (TB) and TcB values above 12 mg/dL (205 μmol/L), resulting in TcB nomograms that underestimate TB levels >12 mg/dL (205 μmol/L). Despite the numerous studies to improve jaundice diagnosis in the past 30 years, there has been a relapse in readmissions, bilirubin encephalopathy, and kernicterus. These trends point towards the need, more than ever before, for improved diagnostic methods, and to treat physiological conditions safely and comfortably in home and hospital settings.

In the current liability-focused environment, hospitals have started adapting cost containment strategies, such as managed care, resulting in a continued trend toward a shorter length of stay for patients. Early discharge has had a potential effect on the efficacy of neonatal screening causing increased readmissions due to jaundice. Patient and provider convenience is a contributing factor to the increasing rate of late-preterm delivery.

Prompt and accurate estimation of bilirubin levels can help offset the damage caused by readmission, but the laboratory techniques used in hospitals have several deficiencies, listed below, that prevent them properly managing the complications in neonates, especially jaundice.

A large contribution to error in any test results comes from pre-analytical errors and bilirubin tests are more sensitive: When a sample is drawn there is no continued metabolism that will cause a change in the bilirubin concentration. However, it is well known that bilirubin in a sample can be degraded by exposure to light, which is also used as treatment of hyperbilirubinemia. Irradiation of a serum sample changes the structure of the bilirubin molecule into several different polar (water-soluble) photoproducts. Some studies have shown that in vitro bilirubin may be degraded up to as much as 50% by light degradation. Additionally, the sampling site for bilirubin testing can result in further discrepancies. Even though there is no agreement in the literature as to whether there is any difference in relation to the choice of sampling site, capillary sampling is preferred as it ensures that only small sample volumes are obtained to avoid iatrogenic anemia, but it also introduces additional pre-analytical factors.

One study reports that out of all the participating laboratories, over 60% of laboratories are using the diazo diagnostic methods. The diazo methods come with numerous drawbacks, many of which stem from the interference caused by other proteins present in the heme during direct spectroscopic measurement as well as the pH dependency. Further, the reagents used with these methods can be troublesome to work with, often having poor stability and requiring several volume transfers, which may lead to inaccurate results. Additionally, the methods can be relatively slow, often requiring 30 minutes or more to provide the total serum bilirubin measurement after initiation.

Other less popular methods include enzymatic methods, HPLC, and direct spectroscopy, and each come with unique drawbacks. For example, enzymatic methods often use bilirubin oxidase which is hard to immobilize, unstable, and rather expensive. Regarding HPLC, traditional methods use an assay setup that is expensive, bulky, and complex. Direct spectroscopy methods often require dilutions in order to correct for interference from hemoglobin, carotenoids, and turbidity. Additionally, direct spectroscopy cannot be automated and consequently is limited in clinical application. With the above technologies, the measurement apparatuses are difficult to minimize which has limited their abilities to provide point-of-care (POCT) testing for bilirubin.

The initiation of jaundice treatment depends on the bilirubin levels, which in previous laboratory tests, has required significant levels of blood, has the risk of sample compromise, labor intensive, and time consuming. Although, jaundice is benign, as its part of the physiological evolution process of neonate's hepatic system, incorrect or delayed diagnosis could lead to severe brain damage like cerebral palsy or kernicterus.

Operational inefficiencies in current clinical systems heavily revolve around administrational activities in patient management. Progressive steps towards tackling the situation can be addressed by embracing new technology in order to overcome pain points that include lack of efficiency, avoidable admissions and readmissions, medical errors, defensive practice, communication, and excessive administrative services. Point of care technology is one of the many technological advances that has the potential to reduce operational inefficiencies, improve the patient monitoring, and diagnostic accuracy. This is especially true in the case of neonatal jaundice, where prompt management is essential to prevent disorders such as neurological induced dysfunction (BIND) and kernicterus.

In short, total serum bilirubin is an important clinical measurement in hepatobiliary disorders and haematological disorders; the importance of bilirubin is underlined by the numerous efforts to measure in a clinical setting including spectrophotometry, HPLC, fluorometry, and enzymatic methods. As noted above, these methods have several disadvantages such as excessive sample preparation, time-consuming analyses, interferences, and instability of reagents. Furthermore, these methods need to be performed with consideration of the photosensitivity of the bilirubin which can critically underestimate bilirubin levels if not sampled in the absence of light.

SUMMARY OF THE DISCLOSURE

The present disclosure addresses the aforementioned drawbacks by providing systems and methods for electroanalytical measurement of bilirubin in a sample from a subject. These systems and methods are able to provide a simpler, faster, and more robust measurement when compared to traditional bilirubin assay methods. The sample may be cooled, transported, prepared, and analyzed using a simple system, thereby eliminating the largest source of error caused by manual handling and sample preparation. The system has an extended shelf life, is easier to use, and is more economical than most of the previous bilirubin assays. The system and methods may be used to provide point-of-care testing of bilirubin in a subject.

In one aspect, the present disclosure provides a method for measuring bilirubin levels in a subject. The method can comprise providing a sample to be measured from the subject, wherein the sample comprises bilirubin bound to albumin; adding a release agent to the sample, the release agent configured to release the bound bilirubin from the albumin; measuring electrochemical data of the sample using an electrochemical cell; and determining a total serum bilirubin concentration of the sample using the electrochemical data.

In another aspect, the present disclosure provides a method for diagnosing a subject based on electrochemical detection of analytes. The method can comprise providing a blood sample to be measured from the subject, wherein the sample comprises both unbound bilirubin and bilirubin bound to albumin; adding a release agent to the sample, the release agent configured to release the bound bilirubin from the albumin; measuring electrochemical data of the sample using an electrochemical cell; determining concentrations of conjugated bilirubin, unconjugated bilirubin, total serum bilirubin and albumin using the electrochemical data; and making a diagnosis of an illness for the subject based on the determined concentrations of conjugated bilirubin, unconjugated bilirubin, and albumin In yet another aspect, the present disclosure provides a system for electrochemical detection of analytes. The system can comprise a cartridge comprising a receiving zone configured to receive a sample, wherein the sample comprises bilirubin bound to albumin; a preparation zone holding a release agent and configured to receive the sample from the receiving zone and combine the sample with the release agent in order to release the bound bilirubin from the albumin; and a sensing zone having multiple electrodes and configured to receive the sample from the preparation zone and provide electrical energy from the electrodes to a connector. The system can also comprise a device configured to receive a portion of the cartridge, wherein the device comprises a receptacle configured to receive and be in electrical communication with the connector; a controller in electrical communication with the receptacle and configured to: control a potential on at least one of the electrodes; and receive the electrical energy and provide information regarding concentrations of analytes present in the sample.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

As used herein, "total serum bilirubin", also referred to as "total bilirubin", is the union of conjugated and unconjugated bilirubin. Total serum bilirubin level has been described as providing a generally reliable measure of health of a person's hepatic system. Thus, it is often one of the first metabolites measured to evaluate the health of a neonate regarding the risk of hyperbilirubinemia. The decision to initiate phototherapy, or any other course of action regarding hyperbilirubinemia, is often based on the newborn's age and total serum bilirubin level and rate of change of total serum bilirubin level.

Conjugated bilirubin has glucuronic acid moieties that are not present in unconjugated bilirubin. Conjugated bilirubin can be formed in the liver resulting from the hepatic conjugation of unconjugated bilirubin to make it water soluble. There are instances where a subject may have normal levels of total serum bilirubin but excess conjugated bilirubin and δ-bilirubin (collectively called direct bilirubin). Hence, identifying these newborns with cholestasis from the masses of jaundiced newborns can be difficult but is important for early diagnosis and treatment. For this reason, conjugated bilirubin levels are often measured.

This unconjugated form is suspected of being the only form of bilirubin capable of crossing the intact blood-brain barrier. The serum protein albumin binds to unconjugated bilirubin making it less toxic.

The total serum bilirubin (TSB), unconjugated bilirubin ($B_f$), albumin (A), and bilirubin binding capacity (K) are related through equation 1:

$$B_f = \frac{TSB - B_f}{K(A - TSB + B_f)} \quad (1)$$

A common misconception in clinical practice is that the TSB and TSB/Albumin ratio (TSB/A) independently predict kernicterus. In fact, the current American Academy of Pediatrics guidelines for managing healthy jaundiced term and near-term newborns recommends the use of the TSB/A ratio in addition to the TSB. While the ratio is a rough measure of bilirubin-albumin binding and has not been widely used clinically, clinicians have been recently encouraged to measure the albumin levels along with the TSB.

As used herein, a subject may be a living organism. The subject may be a living organism with a liver. The subject may be mammalian. The subject may be a human. The subject may be a neonate.

Although the system and methods of the present disclosure are often described as being intended for use with neonates for diagnosing jaundice, one of skill in the art could envision could envision applying the teachings described herein to a variety of additional applications.

Described herein are systems and methods for electrochemical detection of analytes such as bilirubin derivatives and albumin. In general, electroanalytical methods are used on a sample that has been treated with a release agent to release bound bilirubin from albumin.

Figure 1:
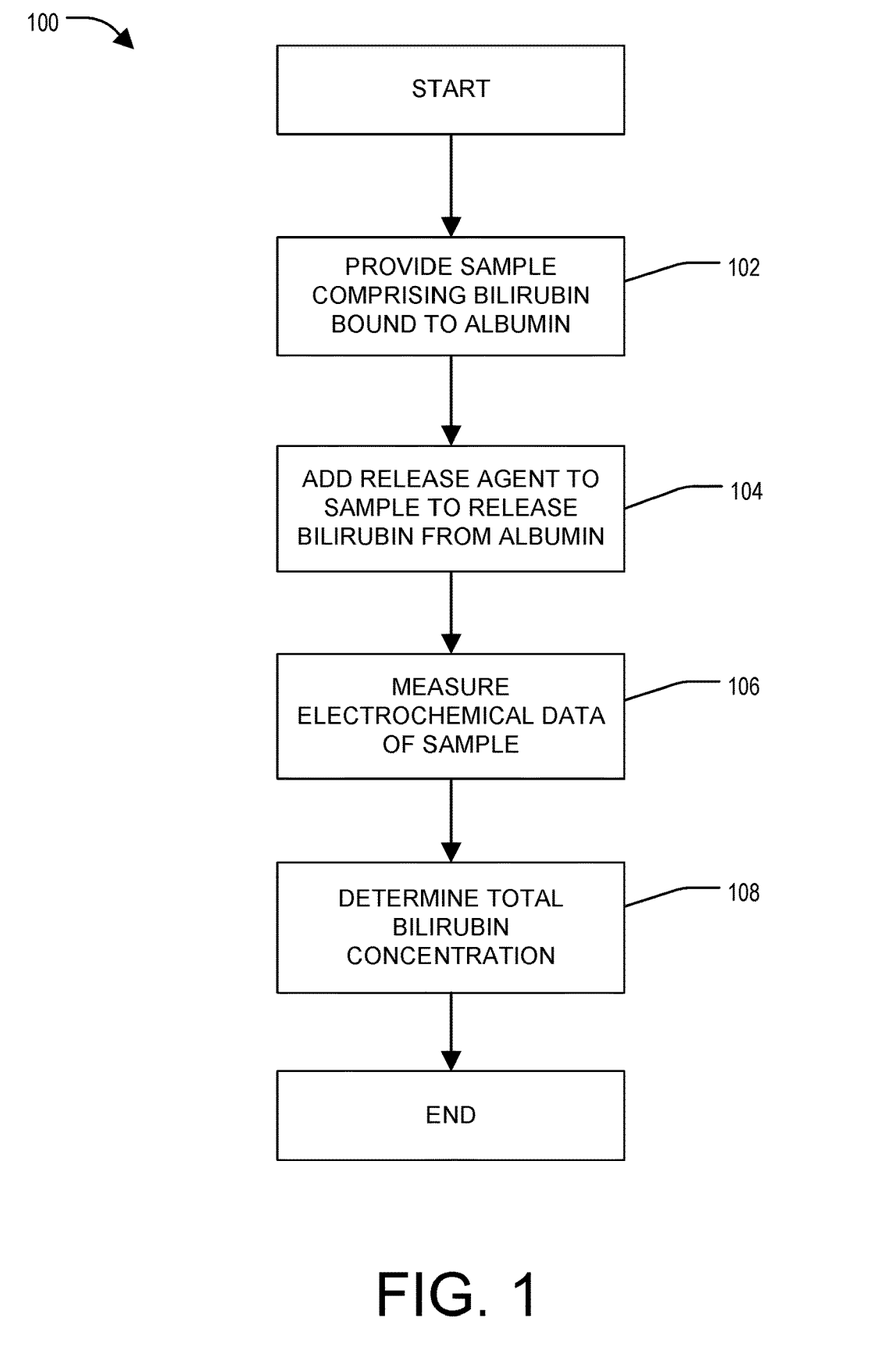
FIG. 1 depicts a flowchart of a method for measuring bilirubin levels in a subject, in accordance with one aspect of the present disclosure.

FIG. 1 depicts a flowchart 100 of a method for measuring bilirubin levels in a subject. The flowchart 100 comprises a first step 102 of providing a sample comprising bilirubin bound to albumin. The sample may be a bodily fluid, tissue sample, or excretion from the subject. For example, the sample may be a blood sample of the subject. The blood sample may be whole blood or separate blood. The sample may also be plasma, serum, or cerebral spinal fluid (CSF). Such a sample may be treated or untreated prior to being provided. The blood sample may be provided within a short period of time after being acquired from the subject, for example the blood sample may be provided within 60 seconds of being drawn from the subject. The blood sample may have a volume less than 100, 50, 40, 30, 20, 10, 7, 4, or 2 microliters or less.

The flowchart 100 comprises a second step 104 of adding a release agent to the sample, the release agent configured to release the bound bilirubin from the albumin. The release agent may release the bound bilirubin by means of competitive inhibition. The release agent may release additional molecules bound to albumin that are not bilirubin derivatives. The release agent may be 4,4'-(1,1-dioxido-3H-2,1-benzoxathiole-3,3-diyl)bis(2,6-dibromophenol), also referred to as bromophenol blue. Other suitable release agents include, without limitation, cocoamidopropyl sulfobetaine, CHAPS (3-[3-Cholamidopropyl)-dimethylamminonio]-1-propanesulfonate), CHAPSO (3-[3-Cholamidopropyl)-dimethylamminonio]-2-hydroxy-1-propanesulfonate), cocoamidopropyl betaine, caffeine, sodium benzoate, sodium acetate, ethylene glycol, hexadecanoic acid, (9Z)-octadec-9-enoic acid, haematin, sulfonamides, salicylate, sodium dodecyl sulfate, 4,4'-(1,1-dioxido-3H-2,1-benzoxathiole-3,3-diyl)bis(2,6-dibromophenol).

The release agent may be in the form of a dry solid prior to being added to the sample. Alternatively, the release agent may be formed as a non-dry solid or a fluid (e.g. a gas or a liquid). The amount of release agent may be dependent on the concentration of the sample and the expected clinical range of bilirubin. For example, a 1 to 3 equivalent molar concentration of the release agent relative to the upper limit of the expected clinical range of bilirubin may be used.

The sample may undergo additional treatments prior to the measurement step. For example, the sample may be filtered to remove particles above a certain size. Additional agents may be added to the sample. These additional agents may include a surfactant, buffer, salt, second release agent, or mixtures thereof. If a surfactant is added, the surfactant may comprise sodium dodecyl sulfate or CHAPS (3-[3-Cholamidopropyl)-dimethylamminonio]-1-propanesulfonate). If a buffer is added, the buffer may comprise a phosphate buffer or tris(hydroxymethyl)aminomethane. If a salt is added, the salt may comprise sodium chloride, potassium chloride, sodium hydroxide, a similar salt, or any combinations thereof. The second release agent may be any component previously listed for the release agent. These additional agents may be in the form of dry solids. The additional agents and the release agent may be added to the sample sequentially. In other words, the dissolution of these additional agents can be distinct or overlapping with respect to time. Because some agents could be intrinsically incompatible if formulated together or stored in direct contact, adequate physical separation may be needed in order to prevent interaction, reaction, or degradation during storage.

The flowchart 100 comprises a third step 106 comprising measuring electrochemical data of the sample using an electrochemical cell. The electrochemical data may be potentiometric, coulometric, or voltammetric data. For example a voltage may be varied over time and the resulting current through the sample may be measured. The electrochemical cell may comprise a plurality of electrodes. For example, there may be three electrodes: a working electrode, a second electrode, and a reference electrode. A portion of the sample containing the release agent may contact each electrode. This detection of the measurement of the sample may be either by destructive or non-destructive means. The temperature of the sample may be actively controlled between 20 and 40 degrees Celsius while the step of measuring the electrochemical data is occurring.

The flowchart 100 comprises a fourth step 108 comprising determining a total serum bilirubin concentration of the sample using the electrochemical data. The total serum bilirubin may be measured directly or calculated by first determining the concentration of all bilirubin derivatives. Each analyte concentration may be determined from a specific electrical energy measured in the electrochemical cell. For example, a bilirubin derivative may be known to oxidize near a specific voltage, therefore the measured current near this voltage may correspond to the concentration of the specific analyte in the sample.

Figure 2:
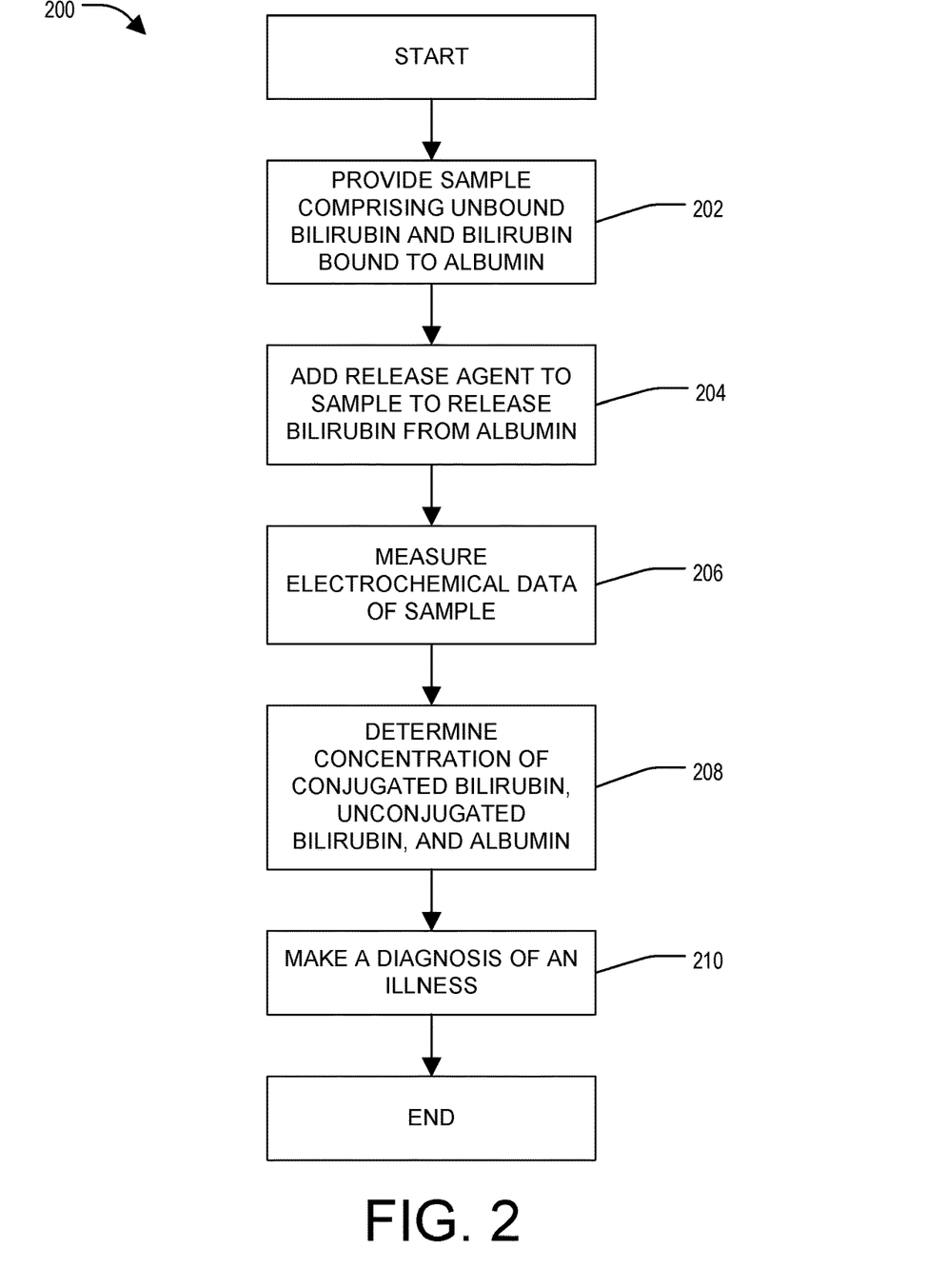
FIG. 2 depicts a flowchart of a method for diagnosing a subject based on electrochemical detection of analytes, in accordance with one aspect of the present disclosure.

FIG. 2 depicts a flowchart 200 for a method for diagnosing a subject based on electrochemical detection of analytes. The method can comprise a first step 202 of providing a blood sample to be measured from the subject, wherein the sample comprises both unbound bilirubin and bilirubin bound to albumin. A second step 204 comprises adding a release agent to the sample, the release agent configured to release the bound bilirubin from the albumin. A third step 206 comprises measuring electrochemical data of the sample using an electrochemical cell. A fourth step 208 comprises determining concentrations of conjugated bilirubin, unconjugated bilirubin, and albumin using the electrochemical data. A fifth step 210 comprises making a diagnosis of an illness for the subject based on the determined concentrations of conjugated bilirubin, unconjugated bilirubin, and albumin.

The method steps provided in 202, 204, 206, and 208 may use any of the techniques or reagents described above for the method flowchart 100. The illness diagnosed may be icterus. The diagnosis may provide a quantification of the severity of the illness. Similar to the step of diagnosing, the method may alternatively include a step of identifying a human subject as having increased risk of hyperbilirubinemia. Once diagnosed or identified, the method may further comprise providing a treatment to the subject. The treatment may comprise phototherapy, intravenous immunoglobulin transfusions, or exchange transfusions. One example of a phototherapy device is described in U.S. patent application Ser. No. 15/143,227, which is incorporated herein by reference.

The illness diagnosed may alternatively be a prediction of stroke; a prediction of the development of Type II Diabetes; a prediction of the development of adverse cardiac events such as hyper-tension related heart-failure; a prediction of the development of Acute Respiratory Distress Syndrome (ARDS) in sepsis; a diagnosis of decreased hepatic uptake; a diagnosis of decreased bilirubin conjugation (decreased hepatic glucuronyl transferase) such as in Gilbert syndrome, Crigler-Najjar Type II, Crigler-Najjar Type I, and neonatal jaundice; a diagnosis of acquired transferase deficiency such as drug inhibition (chloramphenicol pregnanediol), breast milk jaundice, hepatocellular disease like hepatitis and cirrhosis; a diagnosis of sepsis; a diagnosis of blood disorders such as hemolysis intra and extra vascular, erythroblastosis fetalis, and ineffective erythropoiesis; a diagnosis of hereditary disorders due to impaired hepatic excretion such as Dubin-Johnson syndrome, Rotor syndrome, and recurrent intrahepatic cholestasis; a diagnosis of acquired disorders due to impaired hepatic excretion such as hepatocellular diseases like hepatitis and cirrhosis, drug induced cholestasis, alcohol liver disease, sepsis, postoperative state, and biliary cirrhosis; or a diagnosis of disorders due to extrahepatic biliary obstruction such as gallstones, biliary malformation, infection, malignancy, hemobilia, sclerosing cholangitis, and pancreatitis.

Figure 3:
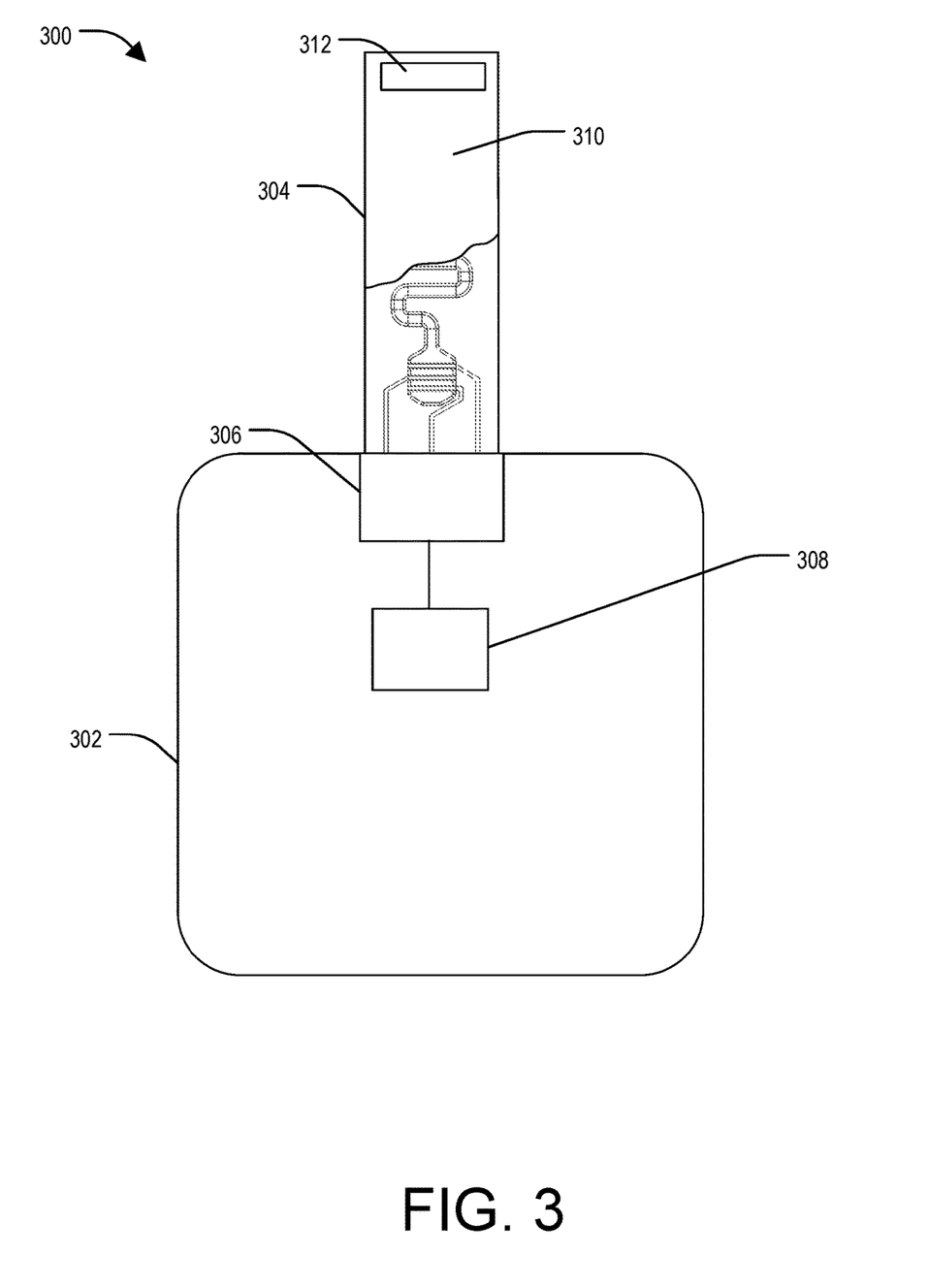
FIG. 3 depicts a system for electrochemical detection of analytes, in accordance with one aspect of the present disclosure.

FIG. 3 depicts a system for electrochemical detection of analytes. The system comprises a device 302 configured to receive a portion of a cartridge 304, wherein the device comprises a receptacle 306 configured to receive and be in electrical communication with a connector (not depicted for clarity reasons) of the cartridge 304; a controller 308 in electrical communication with the receptacle and configured to: control a potential on at least one of the electrodes; and receive electrical energy and provide information regarding concentrations of analytes present in a sample. In this depiction, some internal elements are depicted as visible for clarity reasons. For example, a portion of a top surface 310 of the cartridge 304 has been depicted as transparent.

Although not depicted in FIG. 3, the device 302 may have additional components configured to measure a temperature of a sample in the cartridge 304 and control the temperature of the sample to be maintained between 20 and 40 degrees. For example, the device 302 may have an integrated heater and thermometer. The cartridge top surface 310 may be made of material with a thermal conductivity that allows the device 302 to maintain a roughly uniform temperature at various zones of the cartridge 304. Temperature control may improve assay accuracy and allow the device 302 to be used in ambient conditions where conventional assays have traditionally been limited. The temperature may be controlled relative to ambient temperature. The temperature of the sample may be automatically adjusted by the controller 308 to maintain various zones of the cartridge 302 at specific temperatures.

The device 302 may have additional components that improve its ability to provide information regarding the concentrations of the analytes. For example, the device 302 may be configured to be hand-held. The device 302 may have a graphical user interface, display, battery, wireless communication module, one or more input ports, one or more output ports, or additional electrical components commonly used. The device may have components for receiving instructional input from a user such as a keyboard, touchpad, or one or more buttons or switches. The device may connect to a cloud infrastructure for data storage and analytics. The device may be configured to record and use the history of analyte concentrations of a patient to allow trend monitoring of the concentrations over time, thereby producing a nomogram. For example, the device may plot the hour specific TSB levels against gestational age (nomogram) in the subject. The rate of rise of bilirubin can help guide the efficacy of the treatment to be administered for any form of hyperbilirubinemia.

The receptacle may be a slot or hole of similar shape to the cartridge. The receptacle may be electrically connected to the controller and have components configured to contact the connector of the cartridge and provide electrical communication between the controller and the cartridge.

The cartridge 304 may have an external identifier 312. The external identifier may provide information regarding date of manufacturer or batch number of the cartridge. This information may be used with a time-based algorithm to account for any cartridge aging effects. This time-based algorithm may be used to account for the errors caused by cartridge variability within batches and between batches by using calibration factors determined during the device's manufacturing. Further, any changes in the sensitivity of the device due to aging can be calibrated for by a time-based aging model whose input may be the age of the device since manufacture.

Figure 4A:
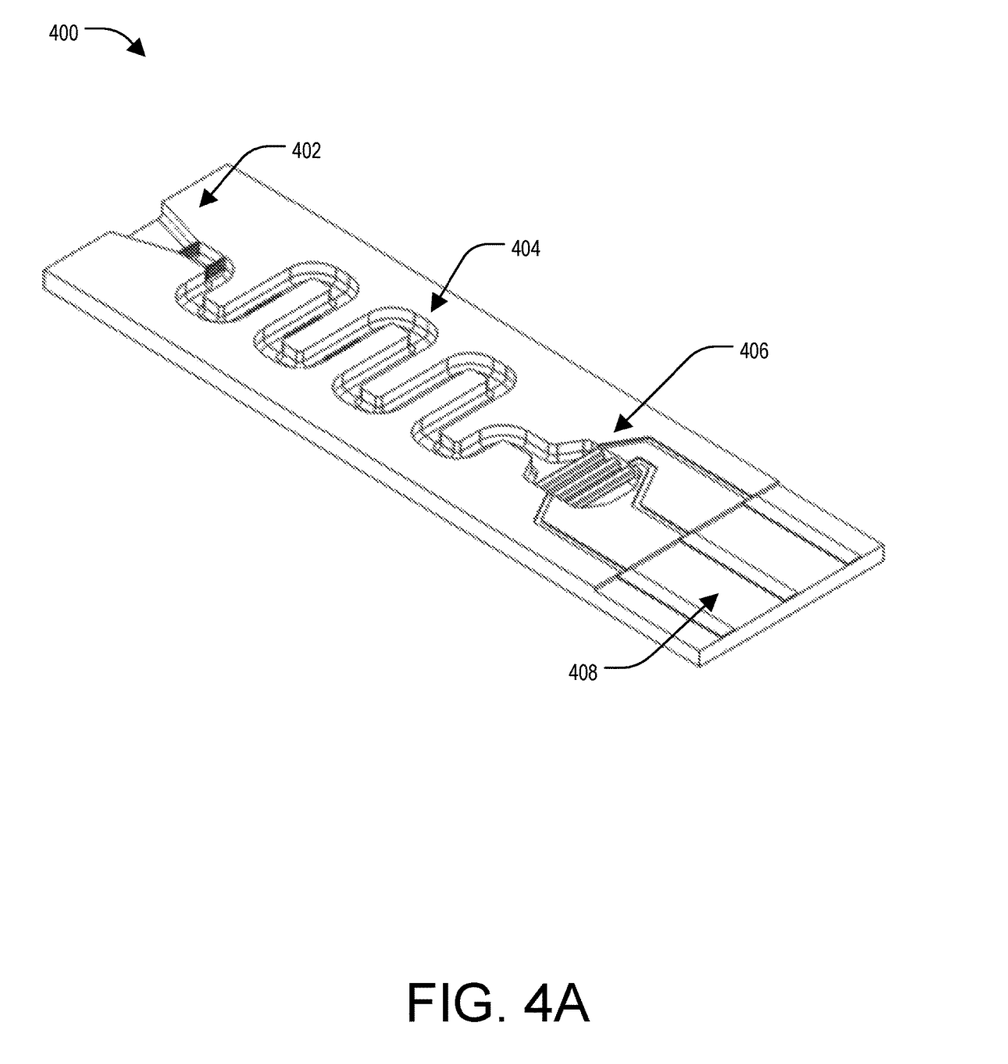
FIG. 4A depicts a perspective view of a cartridge to be used in a system for electrochemical detection of analytes, in accordance with one aspect of the present disclosure.

FIG. 4A depicts a perspective view of a cartridge 400 to be used in a system for electrochemical detection of analytes. The cartridge 400 generally comprises a receiving zone 402 configured to receive a sample, wherein the sample comprises bilirubin bound to albumin; a preparation zone 404 holding a release agent and configured to receive the sample from the receiving zone 402 and combine the sample with the release agent in order to release the bound bilirubin from the albumin; and a sensing zone 406 having multiple electrodes and configured to receive the sample from the preparation zone and provide electrical energy from the electrodes to a connector 408.

Figure 4B:
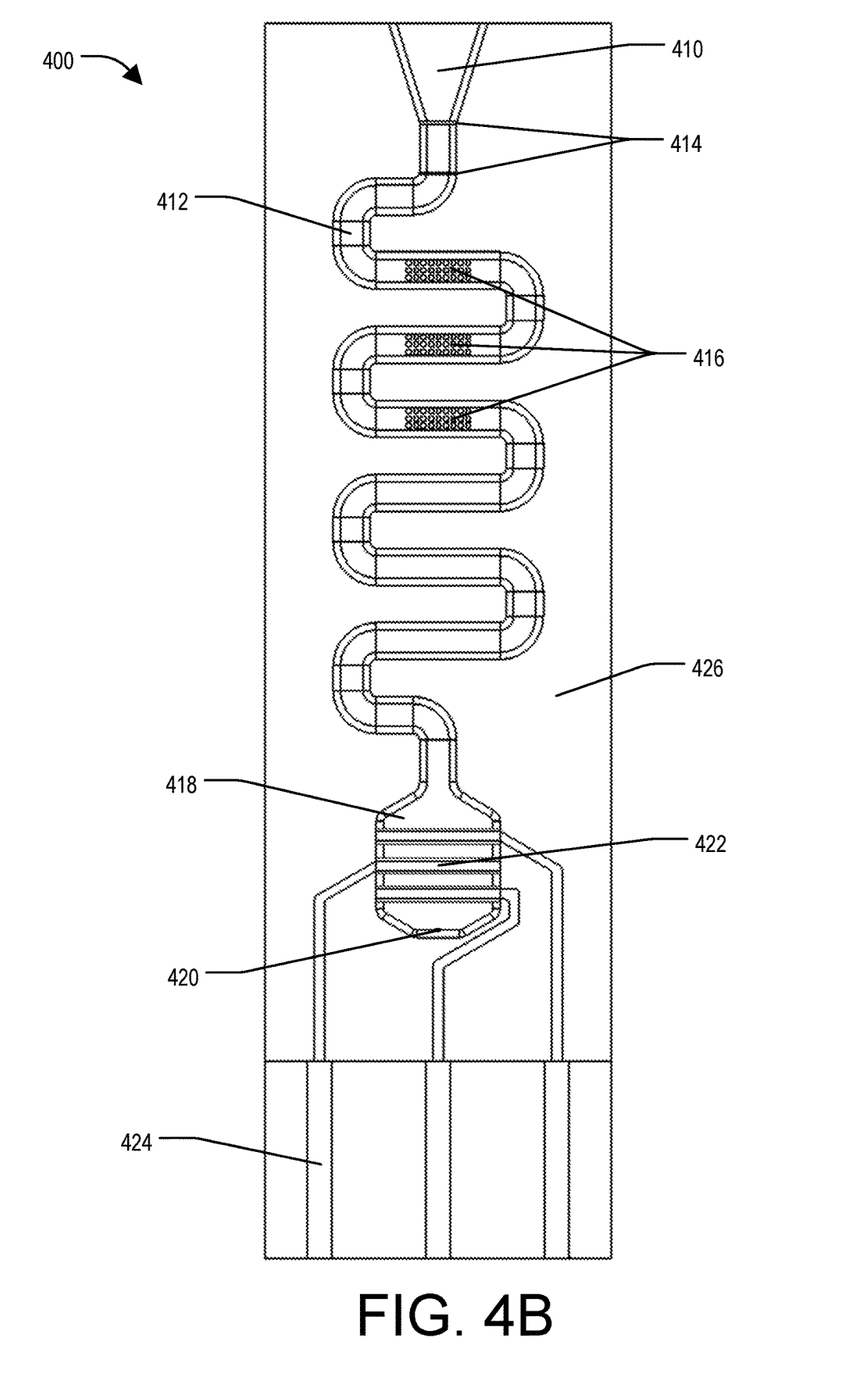
FIG. 4B depicts a top view of the cartridge.

FIG. 4B depicts a top view of a cartridge 400 to be used with a system for electrochemical detection of analytes. The cartridge 400 has an inlet aperture 410 within the receiving zone, which may be tapered or whose surface may be specifically functionalized to improve the transmission of fluid into the preparation zone. For example, the surface contacting the sample may be coated with hydrophilic adhesive, polyester, or polymethyl methacrylate (PMMA). This inlet aperture 410 is connected to a fluid pathway 412 which defines a portion of the preparation zone and fluidly connects the receiving zone to the sensing zone. The fluid pathway 412 comprises multiple filters 414. Chemical agents 416 are also present within the fluid pathway 412. The sensing zone has a cavity 418 that has an air vent 420. The cavity 418 has three electrodes 422 which are electrically connected to three respective connector electrodes 424 of the connector. The cartridge 400 has a body 426 which serves to define the exterior shape as well as the various internal components.

The device and cartridge may use any method variation described herein in order to achieve electrochemical detection of analytes. The analytes may be total bilirubin, conjugated bilirubin, unconjugated bilirubin, and albumin. The inlet aperture may be configured to directly contact a blood sample, such as a blood drop.

Once a sample has been received by the receiving zone 402, it may travel via capillary action through the fluid pathway of the preparation zone to the sensing zone. Any surface of the fluid pathway that contacts the sample may be functionalized to assist the flow of blood. The surface may be specifically functionalized to allow the measurement of the sample to occur before the onset of phenomena such as blood coagulation. The fluid pathway may have dimensions that are designed to control whether flow is turbulent or laminar. The fluid pathway may be a channel or tube having a width of less than about 5 millimeters and a height of less than about 1 millimeter. The fluid pathway dimensions may be sized to reduce the total sample volume necessary for the detection, whilst remaining at a scale that allows for mass production. The length of the tube may be determined to allow for sufficient cooling and preparation of the sample.

As the sample travels through the preparation zone, it may be filtered and have chemical agents added. The filtering may be through size exclusion to remove gross debris and biochemical contaminants. For example, a size-exclusion membrane may be used to block any free hemoglobin reaching the sensing electrodes. Additionally, small molecules such as ascorbic acid may be blocked using membranes such as cellulose acetate. The filtering may be a functionalized surface configured to remove specific components from the sample.

The release agent and any additional agents may be added to the sample either in parallel or sequentially. The dissolution of these reagents can be distinct or overlapping in respect to time. These agents may be dry formulated, lyophilized, or immobilized within films in order to improve shelf life and stability of the system. The shelf life of the system may be longer than 30 days. The agents may also be printed along the channels using analogue/screen printing or digital printing methods. The timing of dissolution of these agents may be controlled through the manufacturing process where the print size and distribution of chemical agent prints is optimized to ensure the correct timing of agent additions.

The total serum bilirubin can be detected in the final sensing chamber by the use of a single or plurality of electrochemical assays. After a short period of time, and upon adequate sample reaching the sensing zone an assay or measurement can take place upon the sample. The initiation of the measurement may be automated by a start condition which can be an electrical signal produced by applying a voltage between electrodes, and a current that runs when the electrodes are shorted by the sample. Alternatively, the measurement can be initiated by the generation of voltage when the blood sample flows between electrodes. The controller may provide this voltage by controlling the potential on at least one of the electrodes. A single sensing zone could be capable of measuring more than one analyte or characteristic of the blood sample either in parallel or sequentially. The cavity of the sensing zone may have a volume of less than 10, 7, 4, or 2 microliters. There may be multiple sensing zones, each configured to provide alternative electrical information. Such multiple sensing zones may be connected to respective multiple preparation zones which differ in the concentrations or specific chemical agents they hold.

The sensing zone may have multiple electrodes. There may specifically be three electrodes. The electrodes may comprise carbon electrodes. The electrodes may comprise multi-walled carbon nanotubes, single-walled carbon nanotubes, or graphene. The use of electrode materials such as carbon can advantageously reduce the oxidation of interferences relative to more catalytic materials such as platinum. Each of the electrodes in the sensing zone may be electrically connected to respective connector electrodes located at the connector. The connector electrodes may comprise any conductive material known in the art. The connector may be shaped to be inserted or attached to the receptacle of the device in a manner that allows electrical connection between the electrodes and the device.

Once the electrical energy is received at one or more of the electrodes and transferred to the device it may be used by the controller to provide the concentrations of the analytes. Similar to the methods described herein, a voltage may be varied over time and the resulting current through the sample may be measured. The electrical energy received may be calibrated relative to other signals including: ambient temperature, sensing zone temperature, or ionic concentration, which may be simultaneously measured. The measurements can be calibrated relative to a number of other inputs including dissolved reagents and calibration factors integrated into the cartridge and determined during the manufacturing process. Further, the errors caused by sensor variability within batches and between batches may be removed both through device characterization at the point of use and also by calibration factors determined during the device's manufacturing.

The concentrations may be provided on a display of a device or transferred to a remote system capable of monitoring the progression of the analyte concentrations over time; capable of conducting analytics to improve prognosis of potential sequelae; capable of presenting the concentrations in numerical and graphical formation; and/or capable of exporting data and results in desired format. The body of the cartridge may have a low flexural modulus. The body of the cartridge may comprise a polymer.

The system described herein provides several advantages over previous bilirubin detection systems. The system requires minimum interventions by a user, therefore removing one of the biggest sources of inaccuracy due to user error when performing bilirubin measurements. In addition, by using electrochemical detection the system and methods provide faster measurements and has improved shelf life stability of reagents used for the measurement. Further, the sample does not leave the device from reception to final detection, therefore eliminating the risk of sample contamination or sample loss. Similarly, concerns regarding cross-contamination between samples are eliminated as the cartridge may be disposed of after measurement of a sample. Because the operation of the device is very rapid, the sample prevented from being degraded by light exposure. Finally, the system is capable of offering the above mentioned advantages right at the patient bedside, or in remote clinics that do not have immediate access to chemistry analyzers.

The systems and methods described herein are capable of measuring bilirubin derivatives as well as albumin concentrations and can therefore allow for improved accuracy when diagnosing neonatal jaundice. Quantifying the levels of these analytes can give practitioners a holistic perspective of the state of jaundice in a neonate or other subject.

EXAMPLES

The following Examples are provided in order to demonstrate and further illustrate certain embodiments and aspects of the present disclosure and are not to be construed as limiting the scope of the disclosure.

Example 1

An experiment was performed to determine the effectiveness of electrochemical detection of albumin, conjugated bilirubin, unconjugated bilirubin, and total serum bilirubin using a release agent such as bromophenol blue.

All electrochemical experiments were performed on screen-printed carbon electrodes with an Ag/AgCl reference electrode in a 3-electrode mode of operation. Cyclic Voltammetry parameters were controlled via a computational program; scan rate: 0.1 V/s, start potential: −0.5V, switch potential: 0.9V, end potential: −0.5V.

Bilirubin (mixed isomers), Fatty-acid free Human serum albumin, Bilirubin conjugated ditaurate disodium salt, Sodium hydroxide, Tris(hydroxymethyl)aminomethane, Hydrochloric acid, Tetrabromophenol Blue were purchased from Sigma Aldrich, UK. Deionized water (resistivity 18.2MΩ cm) was used in the preparation of solutions. Bilirubin was dissolved in 0.05M sodium hydroxide to prepare 1 mM stock and gently vortexed till homogenously mixed. This stock solution was then diluted using 0.05 M Tris-HCl (pH 8.5) to the desired working concentration. Human serum albumin was prepared in 0.05M Tris-HCl (pH 8.5) and vortexed till homogenously mixed. Bromophenol blue was prepared in 0.05M Tris-HCl (pH 8.5). Conjugated bilirubin was dissolved in 0.05M Tris-HCl (pH 8.5) and mixed till homogenous. All tubes containing bilirubin were protected from light.

Regarding the detection of unbound unconjugated bilirubin, it was diluted to a physiologically relevant concentration (100 μM) and analyzed by cyclic voltammetry. Unconjugated bilirubin exhibited a broad anodic peak $E_{pa}$=0.15V, demonstrating that unconjugated bilirubin could be directly oxidized on bare carbon electrodes in the solvent-free system. No cathodic peak was observed, thereby indicating irreversible oxidation. Also, the peak at 0.15V was noticeably absent in second and third scans. Without being bound by theory, it was suspected that the mechanism of oxidation of bilirubin to biliverdin undergoes a loss of two electrons and two protons. Accordingly, we suspect that the peak at 0.15V could be enhanced by using an electron-acceptor such as ruthenium hexamine or by increasing the concentration of a proton-acceptor such as sodium hydroxide.

Consequently, a range of concentrations of bilirubin were tested to confirm the anodic peak current is concentration dependent. A secondary anodic peak was observed at 0.3V for higher concentrations which became noticeably distinct at concentrations of 50 μM and higher. Without being bound by theory, it was suspected that the secondary anodic peaks can be attributed to the successive conversion of biliverdin to purpurin, then to choletelin, and further to subsequent products.

To further investigate the concentration to peak current correlation the scans were assessed for linearity. As per classical linearity criteria, acceptable linearity was defined as a correlation coefficient close to 1, and y-intercept does not differ significantly from zero. The results showed that at the concentration range of 1.5-10.0 mg/dL, peak height current is linear with concentration. The linearity study was then extended to include physiological and pathophysiological ranges (10.0-170.0 mg/dL). As the oxidation of bilirubin involves the loss of the proton, more alkaline environments promote the oxidation process by removing the proton and promoting the forward reaction. Therefore at bilirubin can be oxidized at lower potentials.

Regarding the detection of albumin-bound unconjugated bilirubin, within human plasma, roughly 99.9% of unconjugated bilirubin is bound to albumin due to the poor water solubility of bilirubin. Preparations of physiologically relevant concentrations of albumin and unconjugated bilirubin were analyzed. It was found that the binding of unconjugated bilirubin to albumin inhibited the direct electrochemical oxidation of unconjugated bilirubin. The distinct unconjugated bilirubin peak $E_{pa}$=0.15V is attenuated when mixed with albumin and was found to be instead replaced with peaks at 0.4V and 0.6V.

The inhibition of bilirubin oxidation by albumin needed to be addressed in order to accurately measure total serum bilirubin. Surfactants, caffeine, sodium benzoate and fatty acids are common solubilizing agents. These agents, in addition to alcohols were suspected of being able to break the salt-linkage between unconjugated bilirubin and albumin and were therefore examined for dissociation capabilities. However, the alcohol was found to interfere with the electro-oxidation process. Bromophenol blue was identified as a suitable agent which could compete with unconjugated bilirubin for the binding sites on albumin and demonstrate compatibility with the electrochemical process. Though bromophenol blue is electrochemically active, its peak was found to be present at 0.64V, distinctly separate from the bilirubin peak at 0.15V. The binding of bromophenol blue to albumin was found to diminish the bromophenol blue peak at 0.64V. This is consistent with the effect of albumin on unconjugated bilirubin oxidation. At equal ratios of albumin to bromophenol blue or unconjugated bilirubin, the albumin can eliminate oxidation of binding partners, presenting only a single broad anodic peak at 0.55V.

To better understand the electrochemical implications of the displacement effect, all three components—unconjugated bilirubin, albumin, and bromophenol blue—were mixed together at varying ratios and assessed by cyclic voltammetry. At equal concentration ratios, no displacement of unconjugated bilirubin was observed, indicated by the absence of the unconjugated bilirubin peak. At ratio where the bromophenol blue is in excess, the liberation of unconjugated bilirubin was evident by a characteristic peak at 0.15V. When the concentration of bromophenol blue was increased two-fold, the peak current was 0.645 μA. However, when the bromophenol blue concentration was increased threefold, the peak current was reduced to 0.347

μA and the characteristic bromophenol blue peak at 0.64V was predominant. The presence of the bromophenol blue peak indicated saturation of albumin binding, resulting in unbound bromophenol blue which is available for oxidation. Next, the concentration of unconjugated bilirubin was doubled against the albumin and bromophenol blue; here the typical broad peak ($E_{pa}$=0.15V) of unconjugated bilirubin was present. The bromophenol blue-specific peak was absent, indicating all the bromophenol blue may have been participating in the displacement of bilirubin. These results provide evidence that even at high concentrations of unconjugated bilirubin, the higher binding affinity of bromophenol blue can displace bilirubin.

Regarding the measurement of conjugated bilirubin, this bilirubin derivative is the water-soluble form which has been glycosylated by the UDP enzyme within the liver. In clinical settings, the conjugated bilirubin measurement is required to determine the albumin-bound bilirubin (unconjugated bilirubin) level from the total serum bilirubin. The cyclic voltammetry results of conjugated bilirubin is similar to that of unconjugated bilirubin, consisting of an anodic peak at 0.15V. Like unconjugated bilirubin, a secondary anodic peak was found to be present at 0.3V indicating successive oxidation of biliverdin. However, unlike the scan of unconjugated bilirubin, the peak at 0.3V was distinct from the first peak. A third anodic peak at 0.44V was exhibited specifically by conjugated bilirubin. This third peak provides an opportunity to directly distinguish conjugated bilirubin from unconjugated bilirubin without the need for a separate analysis.

A linearity study of conjugated bilirubin was then conducted to understand the concentration to peak height relationship across the physiological concentration range of 0.0625 mg/dL to 25 mg/dL. All three peaks were consistently present across all the concentrations tested, therefore conjugated bilirubin and unbound-, unconjugated-bilirubin are clearly distinguishable from one another. The results show that at the concentration range of 0.0625 mg/dL to 20 mg/dL peak height current is linear with concentration.

The interaction of conjugated bilirubin and albumin was investigated with mixtures of conjugated bilirubin and albumin were prepared at equal concentrations. As with unconjugated bilirubin, albumin complexes with conjugated bilirubin, albeit to a lesser degree, and hinders oxidation of bilirubin. This was demonstrated by the diminution of the peak at 0.15V. However, the presence of a small peak at 0.15V does indicate the binding affinity of conjugated bilirubin to albumin is weaker than that of unbound bilirubin. Comparing the voltammetric results, it is clear that some of the conjugated bilirubin did not bind albumin and is available for oxidation. As with the above results, the characteristic albumin peak $E_{pa}$=0.55V was observed.

These results indicate that to ensure the oxidation of conjugated bilirubin, it will likely have to be isolated from albumin. As with unconjugated bilirubin, bromophenol blue was used a competitive binding ligand for the displacement of conjugated bilirubin. These three components—conjugated bilirubin, albumin, and bromophenol blue—were mixed at equal concentrations and analyzed by cyclic voltammetry. At 1:1:1 ratio, the bromophenol blue sufficiently displaced the conjugated bilirubin as evidenced by the peak at 0.15V. Following the peak, the broad scan obscures any successive peaks from either biliverdin, albumin or bromophenol blue.

The liberation of conjugated bilirubin and unconjugated bilirubin differs in their distinctive voltammograms and required concentrations of bromophenol blue. These differences could be used to differentiate between conjugated and unconjugated bilirubin in a single analysis.

Regarding the measurement of albumin, the results showed that albumin was inherently electrochemically active, therefore a range of physiologically relevant concentrations were analyzed by cyclic voltammetry to determine peak height to concentration correlation. It was found that the peak $E_{pa}$=0.55V on the first scan demonstrated linearity with a concentration range of 1 g/dL to 5 g/dL. The linearity study was then extended to include a wider range 0.175 g/dL to 30 g/dL. The cyclic voltammogram of albumin demonstrates that across all concentrations the broad peak at $E_{pa}$=0.6V is present; the peak is more distinguishable at lower concentrations. Albumin maintained good linearity even at relatively high concentrations despite to broadening of the peak. This albumin measurement may be used to supplement the measurement of bilirubin and allow for a more accurate representation of the health of patients to be provided to clinicians.

The present disclosure has described one or more preferred embodiments, and it should be appreciated that many equivalents, alternatives, variations, and modifications, aside from those expressly stated, are possible and within the scope of the invention.

The invention claimed is:

1. A method for measuring bilirubin levels in a subject, the method comprising:
   providing a fluid sample to be measured from the subject to a microfluidic device, wherein the sample comprises bilirubin bound to albumin;
   contacting the fluid sample and a release agent in the form of a dry solid, the release agent configured to release the bound bilirubin from the albumin;
   measuring electrochemical data of the sample using an electrochemical cell, wherein the electrochemical cell comprises screen printed electrodes; and
   determining a total serum bilirubin concentration of the sample using the electrochemical data.

2. The method as recited in claim 1, wherein the fluid sample is an untreated blood sample of the subject.

3. The method as recited in claim 1, wherein the release agent is 4,4'-(1,1-dioxido-3H-2,1-benzoxathiole-3,3-diyl) bis(2,6-dibromophenol).

4. The method as recited in claim 1, wherein the electrochemical data is voltammetric data.

5. The method as recited in claim 1, further comprising adding additional agents to the sample, wherein the addition of the agents occurs prior to the measurement of the electrochemical data.

6. The method as recited in claim 5, wherein the additional agents are in the form of dry solids.

7. The method as recited in claim 5, wherein the additional agents include at least one of a surfactant, buffer, salt, or second release agent.

8. A method for diagnosing a subject based on electrochemical detection of analytes, the method comprising:
   providing a blood sample to be measured from the subject to a microfluidic device, wherein the sample comprises both unbound bilirubin and bilirubin bound to albumin;
   contacting the blood sample and a release agent in the form of a dry solid, the release agent configured to release the bound bilirubin from the albumin;
   measuring electrochemical data of the sample using an electrochemical cell, wherein the electrochemical cell comprises screen printed electrodes;

determining concentrations of conjugated bilirubin, unconjugated bilirubin, total serum bilirubin, and albumin using the electrochemical data; and making a diagnosis of an illness for the subject based on the determined concentrations of conjugated bilirubin, unconjugated bilirubin, total serum bilirubin, and albumin.

9. The method as recited in claim 8, wherein the blood sample is an untreated blood sample of the subject.

10. The method as recited in claim 8, wherein the release agent is 4,4'-(1,1-dioxido-3H-2,1-benzoxathiole-3,3-diyl) bis(2,6-dibromophenol).

11. The method as recited in claim 8, wherein the electrochemical data is voltammetric data.

12. The method of claim 8, wherein the illness is icterus.

13. The method as recited in claim 8, further comprising adding additional agents to the sample, wherein the addition of the agents occurs prior to the measurement of the electrochemical data.

14. The method as recited in claim 13, wherein the additional agents are in the form of dry solids.

15. The method as recited in claim 13, wherein the additional agents include at least one of a surfactant, buffer, salt, or second release agent.

16. The method as recited in claim 8, wherein the temperature of the sample is actively controlled between 20 and 40 degrees Celsius while the step of measuring the electrochemical data is occurring.

17. The method as recited in claim 8, further comprising filtering the sample, wherein the filtering occurs prior to the measurement of the electrochemical data.

18. The method as recited in claim 8, further comprising providing a treatment to the subject, wherein at least one of the type of treatment and intensity of treatment is determined using the diagnosis of the illness.

19. The method of claim 1, wherein the volume of the sample is less than 40 microliters.

20. The method of claim 8, wherein the volume of the blood sample is less than 40 microliters.

* * * * *